United States Patent [19]
Leet et al.

[11] Patent Number: 6,114,576
[45] Date of Patent: Sep. 5, 2000

[54] CARBONYLATION PROCESS WITH INTEGRATED HEAT EXCHANGE

[75] Inventors: William A. Leet, Naperville; Santi Kulprathipanja, Inverness; Bruce A. Briggs, Carol Stream, all of Ill.

[73] Assignee: UOP LLC, Des Plaines, Ill.

[21] Appl. No.: 09/215,734

[22] Filed: Dec. 18, 1998

Related U.S. Application Data

[60] Provisional application No. 60/068,023, Dec. 18, 1997.
[51] Int. Cl.$^7$ .......................... C07C 51/12; C07C 51/10; C07C 51/14; C07C 67/00
[52] U.S. Cl. ..................... 562/519; 562/517; 562/520; 560/204
[58] Field of Search ................................ 562/517, 519, 562/520; 560/204

[56] References Cited

U.S. PATENT DOCUMENTS

| | | | |
|---|---|---|---|
| 3,769,329 | 10/1973 | Paulik et al. | 260/488 K |
| 3,791,935 | 2/1974 | Eubanks et al. | 203/74 |
| 5,227,520 | 7/1993 | Cooper | 562/519 |
| 5,334,755 | 8/1994 | Yoneda et al. | 562/519 |
| 5,364,963 | 11/1994 | Minami et al. | 562/519 |
| 5,374,774 | 12/1994 | Ochiai | 562/519 |
| 5,520,890 | 5/1996 | Lorentzen et al. | 422/197 |
| 5,662,780 | 9/1997 | Sasaki et al. | 203/81 |
| 5,663,430 | 9/1997 | Morris et al. | 562/608 |

FOREIGN PATENT DOCUMENTS 0 846 674 A1  6/1998  European Pat. Off. ........ C07C 51/12

OTHER PUBLICATIONS

Acetic Acid and Derivatives pp. 121–139 *Kirk–Othmer Encyclopedia of Chemical Technology,* $4^4$ Edition, vol. 1, John Wiley and Sons, New York, 1991.

The Chiyoda/UOP Acetica™ Process: A Novel Acetic Acid Technology by Noriyuki Yoneda et al. presented at Third Annual Tokyo Conference on Advanced Catalytic Science and Technology Japan 1998.

"Acetic Acid by Low Pressure Carbonylation of Methanol with a Supported Rhodium Catalyst" by Wing S. Fong, *Process Economics Program,* PEP Review No. 88–3–4, SRI International, Menlo Park, CA, Feb. (1990), pp. 1–14.

*Primary Examiner*—Samuel Barts
*Assistant Examiner*—J. Parsa
*Attorney, Agent, or Firm*—John G. Tolomei; Michael A. Moore

[57] ABSTRACT

A process for the production of a carboxylic acid in the presence of solid catalyst particles that uses the exothermic heat of reaction with high efficiency in recovering the carboxylic acid product is disclosed. This process uses indirect heat exchange to transfer the heat of reaction to another stream, without the need for an additional heat transfer fluid such as steam. This invention is especially applicable to the production of acetic acid.

19 Claims, 2 Drawing Sheets

CARBONYLATION PROCESS WITH INTEGRATED HEAT EXCHANGE

CROSS-REFERENCE TO RELATED APPLICATION

This application claims the benefit of U.S. Provisional Application No. 60/068,023, filed on Dec. 18, 1997.

FIELD OF THE INVENTION

This invention generally relates to producing carboxylic acids with less energy consumption. Specifically, this invention relates to a method of producing carboxylic acids that uses the exothermic heat of reaction with high efficiency in recovering the carboxylic acid product.

BACKGROUND OF THE INVENTION

The production of carboxylic acids by the carbonylation of alcohols with carbon monoxide is well known. One example, the carbonylation of methanol, is the most important reaction for the commercial production of acetic acid. Acetic acid, which is a principal ingredient in vinegar, has hundreds of uses in addition to giving flavor to cooking and salads. Paints and adhesives contain latex emulsion resins polymerized from vinyl acetate monomer (VAM) made with acetic acid, and some cellulosic fibers and plastics are manufactured from acetic anhydride derived from acetic acid.

Carbonylation of methanol to acetic acid is an exothermic reaction. The heat of reaction must be removed in order to control the temperature in the carbonylation reaction zone. The methods by which the prior art processes remove this heat of reaction are exemplified by the teachings of U.S. Pat. Nos. 5,334,755 (Yoneda et al.) and 5,364,963 (Minami et al.). One method, which is used with a continuous flow stirred tank type reactor, comprises feeding a portion of the solution in the reactor to a cooler, which cools that portion of the solution by indirect heat exchange with a cooling medium. The cooled solution is then recycled to the reactor. Another method, which is used with a plug flow type reactor that has a plurality of catalyst-containing pipes, comprises passing the reaction solution through the pipes while passing a cooling medium through the sheath that surrounds the pipes. For this method, the cooling medium is saturated boiler feed water which, after having been heated and vaporized to low pressure steam, may be used as a heat source for a distillation tower that recovers the acetic acid product. Yet another method, which is also used with a continuous flow stirred tank type reactor, comprises installing a cooling coil inside the reactor and passing a cooling medium through the coil.

One of the problems with both of these prior art methods is that the heat of reaction is transferred in two steps, first to a cooling medium, and then from the now-heated cooling medium to some other heat sink. In some prior art processes, the cooling medium cannot transfer any heat to the other heat sink, because the temperature of the cooling medium is less than or equal to the temperature of the other heat sink. In other prior art processes, the temperature of the cooling medium is greater than the temperature of the other heat sink so that in theory heat could be transferred from the cooling medium to the other heat sink. However, in practice heat cannot be transferred because the difference in the temperatures of the cooling medium and the other heat sink is so small that the surface area required to accomplish the heat transfer would be impracticably large and the necessary heat transfer equipment would be prohibitively expensive. Accordingly, even if the other heat sink is a stream within the carbonylation process, this two-step transfer of heat is inefficient because a significant proportion of the heat of reaction in the prior art methods is poorly or inefficiently utilized.

The inefficiency of the prior art methods, which both use a cooling medium, arises in both heat transfer steps. In the first step, the temperature of the cooling medium cannot as a practical matter be heated to the maximum temperature of the reaction solution. Rather, the cooling medium is heated only to a temperature that is less than the maximum temperature of the reaction solution by a temperature difference that is equal to the hot end approach of the heat exchanger that is employed in the first step. The heat of reaction that corresponds to the temperature difference of the hot end approach is left unused and is effectively lost, because it is never transferred to the cooling medium.

Similarly, in the second step, the temperature of the cooling medium cannot as a practical matter be cooled to the minimum temperature of the other heat sink. Instead, the cooling medium is cooled only to a temperature that is greater than the minimum temperature of the heat sink by a temperature difference equal to the cold end approach of the heat exchanger that is employed in the second step. Accordingly, the heat of reaction that corresponds to the temperature difference of the cold end approach is left unused and is also effectively lost, because it is never transferred from the cooling medium.

Taking into account both heat transfer steps, the total unutilized heat of reaction is thus represented by the sum of the hot end approach of the first step and the cold end approach of the second step. If the heat of reaction and/or the difference between the maximum temperature of the reaction zone and the minimum temperature of the heat sink is relatively small, this total unutilized heat of reaction can be a large percentage of the total heat of reaction.

Accordingly, methods of utilizing the heat of reaction in a carbonylation process are sought that use the heat of reaction in a manner that is more efficient than the prior art methods.

SUMMARY OF THE INVENTION

This invention is a process for producing carboxylic acids that uses the exothermic heat of reaction with high efficiency in recovering the carboxylic acid product. Using indirect heat exchange, a stream withdrawn from the reactor or the medium or solution within the reactor is cooled by heating process streams in the product recovery section of the process. This invention uses a process stream as the cooling medium for the indirect heat exchange, thereby dispensing with the need for a separate heat transfer fluid, such as utility boiler feed water or steam. By exchanging the heat of reaction from one stream within the carbonylation process to another stream within the carbonylation process in a single step of indirect heat exchange, this invention provides for greater utilization of the heat of reaction than the prior art processes. Compared to prior art processes, this invention requires less heat transfer surface area for a given amount of heat transferred or exchanges more heat for a given amount of heat transfer surface area.

Accordingly, in one embodiment, this invention is a process for the production of a carboxylic acid. An alcohol and/or a reactive derivative of an alcohol reacts with carbon monoxide in the presence of solid catalyst particles in a reaction zone to produce carboxylic acid. A reaction effluent comprising carboxylic acid is withdrawn from the reaction zone. A first portion of the reaction effluent is cooled in an effluent recycle heat exchanger to produce a recycle stream. At least a portion of the recycle stream passes to the reaction zone. A second portion of the reaction effluent is separated in a separation zone, and a heavy stream comprising carboxylic acid is withdrawn from the separation zone. At least a first portion of the heavy stream is heated by indirect heat exchange in the effluent recycle heat exchanger with the first portion of the reaction effluent to produce a heated heavy stream. At least a portion of the heated heavy stream passes to the separation zone. Carboxylic acid is recovered from the separation zone.

INFORMATION DISCLOSURE

Methods of production of acetic acid are described in the section entitled, "Acetic Acid and Derivatives," at pages 121 to 139 of Volume 1 of *Kirk-Othmer Encyclopedia of Chemical Technology,* Fourth Edition, published by John Wiley and Sons of New York in 1991.

U.S. Pat. Nos. 5,334,755 (Yoneda et al.) and 5,364,963 (Minami et al.) disclose processes for preparing acetic acid by carbonylation of methanol. One process uses a continuous flow stirred tank type reactor, and a portion of the solution in the reactor is withdrawn and fed through a line to a cooler, which cools that portion of the solution by indirect heat exchange with a cooling medium. The cooled solution is recycled to the reactor to maintain the temperature within the reactor at a predetermined range. Another process disclosed in U.S. Pat. Nos. 5,334,755 and 5,364,963 uses a plug flow type reactor that has a plurality of catalyst-containing pipes connected in parallel with each other. The reaction solution flows within the pipes. The pipes are surrounded by a sheath into which a cooling medium such as low temperature steam is supplied for indirect heat exchange. The heated steam may be used as a heat source for a distillation tower that recovers the acetic acid product.

U.S. Pat. No. 5,364,963 (Minami et al.) discloses a heterogeneous methanol carbonylation catalyst that includes a rhodium complex supported on a porous, cross-linked vinylpyridine resin, wherein the vinylpyridine resin has a cross-linking degree of 30–60%, a pore volume of 0.1–0.4 ml/g, and an average pore diameter of 20–100 nanometers (nm). The teachings of U.S. Pat. No. 5,364,963 that relate to the methanol carbonylation catalyst are incorporated herein by reference. U.S. Pat. No. 5,364,963, and U.S. Pat. No. 5,334,755 (Yoneda et al.) teach passing a portion of the effluent from a reactor containing such a catalyst to a distillation tower.

U.S. Pat. No. 5,663,430 (Morris et al.) discloses a methanol carbonylation process that uses a soluble iridium and/or rhodium homogeneous catalyst, with an alkyl halide promoter and an optional co-promoter, wherein the effluent of the carbonylation reactor passes to a flash separation vessel with a scrubbing section with a liquid wash.

U.S. Pat. No. 5,662,780 (Sasaki et al.) discloses an extraction method for purifying an aqueous solution of acetic acid that uses isopropyl acetate as the extracting medium.

U.S. Pat. No. 5,520,890 (Lorentzen, et al.) describes a multi-phase catalytic reactor in which a liquid product is separated from a slurry phase which contains a finely divided solid catalyst in a liquid medium.

U.S. Pat. No. 5,374,774 (Ochiai) describes a control system to control the liquid levels in a reactor-flasher combination used for the carbonylation of methanol to acetic acid using a homogeneous catalyst.

Figure 1:
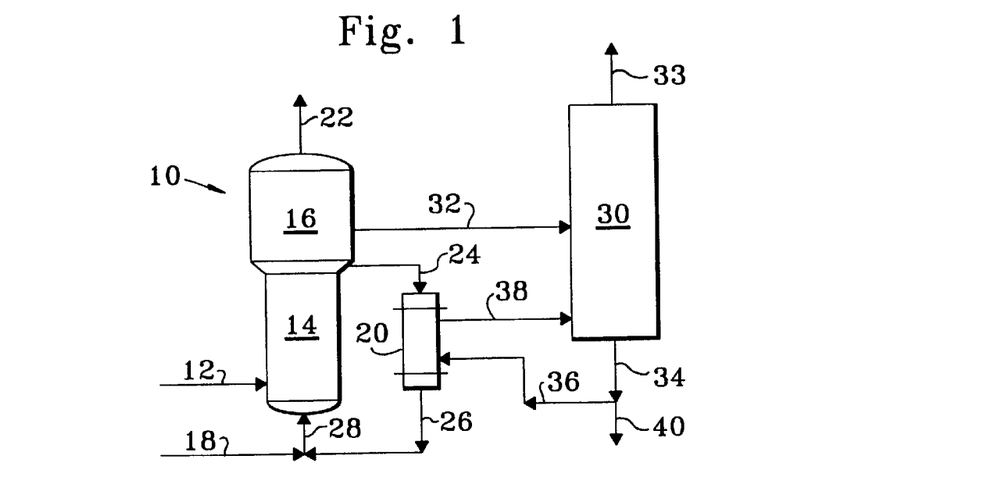
FIG. 1 shows a flow diagram of an embodiment of the invention.

European Patent Application EP-O-846674-A1 discloses a carbonylation process using a homogeneous catalyst for the production of a carboxylic acid that uses two reaction zones and a flash tank with a demister. FIG. 1 of EP-O-846674 shows an optional wash to the flash tank.

The paper entitled "The Chiyoda/UOP Acetica™ Process: A Novel Acetic Acid Technology," by Noriyuki Yoneda et al., which was distributed in association with the Third Annual Tokyo Conference on Advanced Catalytic Science and Technology" held in Tokyo, Japan, on Jul. 19–24, 1988, describes a process for producing acetic acid using a heterogeneous catalyst wherein the carbonylation reactor effluent liquid product is sent to a flash column to remove the crude acetic acid product and reject the carbon monoxide dissolved in the liquid.

U.S. Pat. No. 5,227,520 (Cooper) discloses a process for producing carboxylic acids in which the carbonylation reactor effluent passes to a preliminary flash vaporizer.

PEP Review No. 88-3-4 entitled "Acetic Acid by Low Pressure Carbonylation of Methanol with a Supported Rhodium Catalyst," by Wing S. Fong, in Process Economics Program, pp. 1–14, published by SRI International, Menlo Park, Calif., February 1990, describes a process for producing acetic acid using a heterogeneous-supported rhodium catalyst wherein the crude liquid product stream from the carbonylation reactor is flashed in a flash drum. The flashed vapors, containing acetic acid, water, methyl iodide, formic acid, and propionic acid pass to the purification section of the plant. After a small portion is bled off for catalyst regeneration, the slurry is recycled to the carbonylation reactor.

U.S. Pat. No. 3,769,329 (Paulik et al.) describes a process for the production of acetic acid from methanol in a liquid reaction medium using a homogeneous catalyst consisting essentially of a rhodium compound and a halogen component. The liquid effluent from the reactor passes through a pressure let down valve and is introduced into a distillation or flash column.

U.S. Pat. No. 3,791,935 (Eubanks et al.) describes a process for the purification of carboxylic acid using a homogeneous catalyst, wherein a stream of carboxylic acid to be purified, in either liquid or vapor form, is introduced into a packed, plate, or packed-plate distillation column. The distillation column has provisions for recycle of a portion of the column overhead stream to serve as reflux in the column.

DETAILED DESCRIPTION OF THE INVENTION

The most widely practiced process to which the present invention is applicable is the production of carboxylic acids by carbonylation. The carboxylic acids that can be produced by this invention are carboxylic acids having generally from 2 to 11, preferably from 2 to 6, and more preferably from 2 to 3, carbon atoms. The most preferable carboxylic acid is acetic acid. In addition to being applicable to processes that produce acetic acid primarily or solely, it is believed that this invention is also the applicable to processes that co-produce acetic acid and acetic anhydride, as well as to processes that produce acetic anhydride primarily or solely.

The two feeds of this invention are (i) carbon monoxide and (ii) an alkyl alcohol and/or a reactive derivative of such an alkyl alcohol. Suitable alkyl alcohols include secondary alkyl alcohols, but primary alkyl alcohols are preferred. The alkyl alcohol has one fewer carbon atom than that of the desired carboxylic acid product, and accordingly the alkyl alcohol has generally from 1 to 10, preferably from 1 to 5, more preferably from 1 to 2, and most preferably 1 carbon atom. Among the suitable reactive derivatives of the alkyl alcohol are the alkyl halide derivative that corresponds to replacing the hydroxyl group of the alkyl alcohol with a halogen atom; the ether derivative that corresponds to replacing the hydrogen atom of the hydroxyl group of the alkyl alcohol with the alkyl group of the alkyl alcohol; and the ester derivative that corresponds to replacing the hydrogen atom of the hydroxyl group of the alkyl alcohol with the acetate group of the desired carboxylic acid product. In the production of acetic acid, the preferred alkyl alcohol and reactive derivative thereof are methanol and methyl acetate, respectively.

This invention is broadly applicable to any heterogeneous catalyst, and is not limited to any particular heterogeneous catalyst. Among heterogeneous catalysts, this invention is especially applicable to heterogeneous catalysts comprising a resin, in particular a resin having a strongly coordinating basic nitrogen. Resins having a strongly coordinated basic nitrogen include polymers having pendant quaternized N-base or alkylated N-oxide pyridine groups. The teachings of U.S. Pat. No. 5,360,929 with respect to quaternized N-base or alkylated N-oxide pyridine groups is incorporated herein by reference. These preferred examples of these polymers are poly(2-vinylpyridine), poly(4-vinylpyridine), and poly(vinylpyrrolidone). The resin can also be a copolymer of two or more polymers having pendant quaternized N-base or alkylated N-oxide pyridine groups, such as a copolymer of poly(2-vinylpyridine) and poly(4-vinylpyridine); a copolymer of poly(4-vinylpyridine) and poly(vinylpyrrolidone); and a copolymer of poly(2-vinylpyridine), poly(4-vinylpyridine), and poly (vinylpyrrolidone). In addition, the resin can be a copolymer of polymers having pendant quaternized N-base or alkylated N-oxide pyridine groups and other polymeric building blocks, as exemplified by poly(4-vinylpyridine-co-butyl methacrylate), poly(2-vinylpyridine-co-styrene), poly(4-vinylpyridine-co-styrene), poly(1-vinylpyrrolidone-co-acrylic acid), quaternized poly(1-vinylpyrrolidone-co-2-dimethylaminoethyl methacrylate), and (poly(1-vinylpyrrolidone-co-vinyl acetate). Suitable heterogeneous catalysts for use in this invention are disclosed in U.S. Pat. Nos. 4,328,125 (Drago et al.); 5,155,261 (Marston et al.); and 5,334,755 (Yoneda et al.); 5,364,963 (Minami et al.); and 5,466,874 (Scates et al.).

The preferred catalyst for use in this invention comprises a rhodium complex supported on a porous, cross-linked vinylpyridine resin. It is important that the vinylpyridine resin have a cross-linking degree of 30–60%, preferably 35–60%, a pore volume of 0.2–0.4 cc/g, preferably 0.25–0.4 cc/g, and an average pore diameter of 20–100 nm, preferably 30–90 nm. This catalyst has an improved catalyst life and exhibits high mechanical strengths (e.g. resistance to abrasion and crushing) and high catalytic activity.

When the cross-linking degree of the cross-linked vinylpyridine resin (hereinafter referred to as VP resin for brevity) is less than 30%, the pyridine is apt to be eliminated from the catalyst during use and the abrasion resistance of the catalyst is lowered. Too high a cross-linking degree in excess of 60% is disadvantageous because the catalyst activity is lowered. A pore volume of at least 0.2 cc/g is required for obtaining a desired catalytic activity. When the pore volume exceeds 0.4 cc/g, lowering of the abrasion resistance results. An average pore diameter less than 20 nm causes reduction of the catalytic activity, while an average pore diameter in excess of 100 nm causes the reduction of abrasion resistance.

It is useful at this point to define three additional terms that are used herein. The term "cross-linking degree" herein is defined as follows:

Cross-linking degree(%)=(A/B)×100 wherein A represents the weight of the cross-linking agent contained in the VP resin and B represents the weight of the vinylpyridine monomer units of the VP resin.

The "pore volume" of the VP resin is measured by the mercury penetration method using Mercury Pressure Porosimeter Model 70 (manufactured by Carlo Elba Inc., Italy) with a mercury tension of 474 dyne/cm at 25° C., a contact angle of 140 degrees, and an absolute mercury pressure varying from 1 to 200 kg/cm$^2$.

The term "average pore diameter" used herein is defined as follows:

Average pore volume (nm)=4(C/D)×10$^3$ wherein C represents the pore volume (cc/g) of the VP resin and D represents the surface area (m$^2$/g) of the VP resin measured by the B.E.T. method.

The VP resin may be produced by copolymerizing a vinylpyridine monomer with an aromatic compound having two vinyl groups as a cross-linking agent. The copolymerization method is well known in the art and may be, for example, a method in which a precipitant is added, a method in which a linear polymer is added, a method in which a swelling agent and a precipitant are added, and a method in which a diluent and a linear polymer are added. The method disclosed in Japanese Published Examined Patent Application No. 61-25731 may be particularly suitably used. In this method, a mixture containing a vinyl pyridine monomer, a cross-linking agent having two vinyl groups and, optionally, a vinyl monomer is reacted in the presence of a radical polymerization catalyst, a suspension stabilizing agent, and a precipitant using an aqueous suspension polymerization technique. The stabilizer may be a water-soluble polymer such as polyvinyl alcohol, hydroxyethyl cellulose, carboxymethyl cellulose, sodium polymethacrylate, sodium polyacrylate, starch, gelatin, or an ammonium salt of styrene/meleic anhydride copolymer, or an inorganic salt such as calcium carbonate, calcium sulfate, bentonite or magnesium silicate. The precipitant is an organic liquid which serves to function as a good solvent for the monomer but as a poor solvent for the copolymer produced. Examples of the precipitant includes hydrocarbons having 5–10 carbon atoms such as isooctane, alcohols, and esters. The polymerization degree of the VP resin may be controlled by control of the amount of the cross-linking agent. The pore volume and the average pore diameter may be controlled by selection of the kind and amount of the precipitant. Suitable selection of the kind and amount of the suspension stabilizer and the reaction temperature is also effective to control the pore characteristics of the VP resin.

Illustrative of suitable vinylpyridine monomers for the production of the VP resin are 4-vinylpyridine, 2-vinylpyridine and 2- and 4-vinylpyridine derivatives having a lower alkyl group such as a methyl group or ethyl group on the pyridine ring. The vinylpyridine monomer may be used in conjunction with an aromatic vinyl monomer such as styrene or vinyltoluene. Such a vinyl monomer is used in an amount of 30 mol % or less, preferably 20 mol % or less, based on the total mole of total monomers. Illustrative of suitable cross-linking agents are aromatic divinyl compounds such as divinylbenzene and divinyltoluene and aliphatic divinyl compounds such as butadiene. The amount of the cross-linking agent is determined according to the intended cross-linking degree.

The VP resin is generally used in the form of beads, preferably spheres, having a particle size of 0.01–4 mm, preferably 0.1–2 mm, more preferably 0.4–2 mm. The VP resin is loaded with a rhodium complex [$Rh(CO)_2I_2$] in any suitable manner. The amount of the rhodium complex loaded on the VP resin is 0.2–2% by weight, preferably 0.5–1.0% by weight, in terms of elemental rhodium, based on the weight of the VP resin.

The loading of the VP resin with the rhodium complex may be performed by contacting the VP resin with a rhodium salt in a solvent containing an alkyl iodide under a pressure of carbon monoxide. This method may be carried out by contacting the rhodium salt with the VP resin under conditions as generally adopted in the catalytic carbonylation of methanol. During the course of the above reaction, the pyridine ring of the VP resin are quaternized with the alkyl iodide to form a pyridinium salt to which is ionically bonded a rhodium carbonyl complex [$Rh(CO)_2I_2$] formed by reaction of the rhodium salt, alkyl iodide and carbon monoxide.

Examples of the rhodium salts include rhodium halides such as rhodium chloride, rhodium bromide, and rhodium iodide. Illustrative of suitable alkyl iodides are lower alkyl iodides such as methyl iodide, ethyl iodide, and propyl iodide. The use of methyl iodide is preferred. The alkyl iodide is used in an amount of 2–2000 moles, preferably 5–500 moles, per mole of the rhodium salt. The carbon monoxide pressure under which the rhodium salt is contacted with the VP resin in the presence of the alkyl iodide is 7–30 kg/cm$^2$(g) (100–427 psi(g)), preferably 10–20 kg/cm$^2$(142–284 psi(g)).

The loading of the VP resin with the rhodium complex is preferably performed by a method which includes the steps of:

(a) contacting a solid, pyridine ring-containing resin with an aqueous solution containing rhodium ion so that the rhodium ion is bound to the resin; and (b) contacting said rhodium ion-carrying resin with carbon monoxide and an alkyl iodide in an organic solvent so that the rhodium ion is converted to a rhodium complex bound to the resin.

This method of loading rhodium on the VP resin is also applicable to the production of conventional supported rhodium catalysts. Thus, any know VP resin can be also loaded with the rhodium complex using the method.

In the method to load rhodium on the VP resin, the VP resin is first contacted with an aqueous solution containing rhodium ions so that the rhodium ions are bound to pyridine rings of the resin. The aqueous solution may be prepared by dissolving a water soluble rhodium salt, such as rhodium chloride, rhodium bromide, or rhodium iodide, and preferably has a rhodium concentration of 1000–5000 ppm by weight, more preferably 1500–4000 ppm by weight, in terms of elemental rhodium. The contact of the resin with the aqueous solution may be performed, for example, by immersing the resin in the solution or by passing the solution through a column packed with the resin at a temperature of generally 20°–70° C. (68°–158° F.), preferably 25°–50° C. (77°–122° F.), for a period of time so that desirably 0.2–2% by weight of rhodium ions in terms of elemental rhodium is bound to the resin.

The resin to which rhodium ions have been bound is then contacted with an alkyl iodide and carbon monoxide in an organic solvent so that the rhodium ion bound to the pyridine ring is converted into rhodium complex bound to the pyridinium nitrogen quaternized by reaction with the alkyl iodide.

The alkyl iodide, which is preferably methyl iodide, is used in an amount of generally 2–2000 moles, preferably 50–500 moles, per mole of the rhodium ions bound to the resin. As the organic solvent, there may be used alcohols such an methanol, ethanol, and propanol; carboxylic acids such as acetic acid and propionic acid; esters such as methyl acetate, ethyl acetate, and methyl propionate; and dialkyl ethers such as dimethyl ether. The organic solvent may contain up to 10% by weight of water. The amount of the rhodium ion-carrying resin is generally 2–25% by weight, preferably 5–10% by weight, based on the weight of the organic solvent. The above reaction is generally performed at a temperature of 140°–250° C. (284–482° F.), preferably 160°–220° C. (320°–428° F.) under a partial pressure of carbon monoxide of generally 5–30 kg/cm$^2$(g) (71–427 psi(g)), preferably 10–25 kg/cm$^2$(g) (142–356 psi(g)). The thus obtained rhodium complex loaded resin may be used as such for carbonylation of an alcohol but, if desired, may be separated from the reaction solvent and washed with an organic solvent such as methanol or acetic acid.

In the above method, the VP resin is first contacted with an aqueous solution containing rhodium cation to capture the rhodium cation. Since a rhodium salt is highly soluble in water, no rhodium salt precipitates through this first step. The aqueous solution after contact with the VP resin which still contains unbound rhodium cation can be reused after being added with a supplemental amount of the rhodium salt for adjusting the rhodium concentration. Therefore, all of the rhodium salt can be effectively utilized without loss. In the second step, the rhodium ion-carrying VP resin is reacted with an alkyl iodide and carbon monoxide in an organic solvent. Since the rhodium ion is ionically bound to the pyridine ring of the VP resin, no precipitates of rhodium salt are formed in the organic solvent during the course of the second step.

This preferred catalyst is disclosed in U.S. Pat. No. 5,364,963 (Minami et al.) and is available from Koei Chemical Industry Company, of Japan.

The thus prepared catalyst is advantageously used for the carbonylation of a lower alcohol, especially methanol. Acetic acid is produced by a process which comprises reading carbon monoxide with methanol under a carbon monoxide pressure in the presence of an alkyl iodide and the above catalyst.

The carbonylation of methanol using the above heterogeneous catalyst may be carried out using any desired reactor, such as a fixed bed reactor, an expansion bed reactor, or a stirred tank reactor. The catalyst is placed in the reactor in an amount of, generally, 2–40% by weight based on the weight of the reaction solution contained therein, though the amount varies with the kind of the reactor used. It is recommendable to use the catalyst in an amount of 2–25% by weight in the case of a mixing type reactor, 20–40% by weight in the case of a fixed bed reactor, and 2–25% by weight in the case of an expansion bed reactor, based on the reaction solution contained therein.

As the reaction solution, a carbonyl group-containing compound having at least two carbon atoms is suitably used. Such a compound may be, for example, a saturated aliphatic acid such as acetic acid, propionic acid or butyric acid, an ester such as methyl acetate or ethyl acetate, an aromatic acid such as benzoic acid, or a mixture thereof. The reaction solution can contain up to 50% by weight, preferably 0.1–20% by weight of water. The alkyl iodide is preferably a lower alkyl iodide having 1–6 carbon atoms, such as methyl iodide.

It is preferred that the reaction solution within the reactor have a content of the carbonyl group-containing solvent of at least 0.30 part by weight per part by weight of the methanol present in the reaction solution within the reactor. By using such an organic solvent in such a specific amount, the catalyst can exhibit high catalytic activity and the dissociation of rhodium species from the polymer substrate can be minimized, so that the reaction can be performed at a low carbon monoxide partial pressure. Especially good results are obtainable with the use of the organic solvent in an amount of at least 2.4 parts by weight per part by weight of the methanol.

The term "the reaction solution within the reactor" used herein is intended to mean the solution which is present in the reactor at any point in time in the course of the reaction. Since methanol is consumed as the reaction proceeds, the relative amount of the solvent increases as the reaction proceeds. Thus, in the case of a batch type reactor, for example, the solution may be the raw material feed introduced into the reactor. In the case of a continuous flow, stirred tank-type reactor, the solution may be the product continuously discharged from the reactor. In the case of a piston flow type reactor, the solution may be the whole feed, inclusive of recycled solutions, to the reactor.

The methanol carbonylation is performed at a temperature of 140°–250° C. (284–482° F.), preferably 160°–220° C. (320–428° F.), and a carbon monoxide partial pressure of 7–30 kg/cm$^2$(g) (100–427 psi(g)), preferably 10–20 kg/cm$^2$ (g) (142–284 psi(g)), while maintaining the total reaction pressure in the range of 15–60 kg/cm$^2$(g) (142–854 psi(g)), preferably 15–40 kg/cm$^2$(g) (213–569 psi(g)), more preferably 15–30 kg/cm$^2$(g) (213–427 psi(g)). The alkyl iodide, which is preferably methyl iodide, is used in an amount effective to promote the methanol carbonylation, generally in an amount of 1–40% by weight, preferably 5–30% by weight, based on the weight of the solution within the reactor. The rhodium loaded catalyst is used in a catalytically effective amount, generally in an amount of at least 50 ppm by weight, preferably at least 300 ppm by weight, more preferably at least 500 ppm by weight, in terms of elemental rhodium, based on the weight of the solution within the reactor.

The reaction zone for this invention may be a continuous stirred-tank reactor (CSTR). In a CSTR that uses a heterogeneous catalyst, a stirrer stirs the liquid and keeps the heterogeneous catalyst in suspension in the liquid, provided that the heterogeneous catalyst is finely divided. In addition, the reaction zone for this invention may be a slurry reactor. In a slurry reactor that uses a heterogeneous catalyst, the catalyst must again be finely divided. But in contrast to a CSTR, a slurry reactor is a gas-liquid-solid reactor in which the ascent of gas bubbles through the liquid keeps the heterogeneous catalyst in suspension in the liquid. Also, the reaction zone for this invention may be an ebullated-bed reactor that uses a heterogeneous catalyst. In an ebullated bed, as the term "ebullated bed" is used herein, liquid and gas flow co-currently and upwardly through the reactor, and it is the strong upflow of the liquid that serves to expand the heterogeneous catalyst bed, even though the bed as a whole does not move. The preferred reaction zone for this invention, however, is a three-phase transport reactor (3PTR). A 3PTR is similar to an ebullated bed reactor, except that the upflow of liquid is even stronger. In a 3PTR, the upflow of liquid entrains the heterogeneous catalyst and carries it out of the reactor. At the top of the 3PTR, gas is separated from the slurry of liquid and catalyst, which is recycled to the bottom of the 3PTR. A preferred 3PTR reactor for use in this invention is the reactor disclosed in U.S. Pat. No. 5,536,864 (Paret et al.) when operated with a heterogeneous catalyst. Because the 3PTR is the preferred reactor type, the description which follows will be directed mainly to a reaction zone that is a 3PTR, except where noted. CSTR's, slurry reactors, ebullated bed reactors, and 3PTR's are described in Chapter 9 of the book entitled *Catalytic Reactor Design,* by M. Orhan Tarhan, published by McGraw-Hill Book Company, New York, in 1983.

As mentioned previously, the carbonylation reaction is exothermic, and the heat of reaction must be removed in order to control reaction temperatures. In one embodiment of this invention, the heat of reaction is removed by passing a portion of the reaction solution or the reaction medium through a cooler. As used herein, the term "reaction medium within the reactor" is intended to mean the combination of reaction solution and catalyst particles which is present in the reactor at any point in time in the course of the reaction. The reaction medium generally comprises carbon monoxide, methanol, acetic acid, and solid catalyst particles. In addition, the reaction medium may contain a catalytic promoter, such as an alkyl halide like methyl iodide, which is necessary for some solid catalyst particles. The reaction medium may also contain side reaction by-products such as water and methyl acetate. The presence of methyl acetate can be explained as the corresponding ester that results from the esterification of the alcohol and the product acetic acid. Heavy by-products of side reactions, such as propionic acid and acids having 3 or more carbon atoms, may also be present. As used herein, the term "heavy by-product" means a product of the reaction zone that has one more carbon atom than that of the desired carboxylic acid product. Thus in the production of acetic acid propionic acid and other compounds having three or more carbon atoms are considered to be heavy by-products. Generally, at separation conditions, a heavy by-product has a boiling point that is greater than that of the desired carboxylic acid product. Thus, at normal conditions, propionic acid boils at about 141° C. while acetic acid boils at 118° C.

The stream that is cooled in the cooler may be an aliquot or nonaliquot portion of the reaction effluent. After cooling, the cooled portion is recycled to the reactor. Alternatively, another stream, that is a stream that is distinct and separate from the reaction effluent, may be withdrawn from any suitable location in the reactor. This entire separate stream may be cooled, or an aliquot or nonaliquot portion of the stream may be cooled. After cooling, the cooled stream or portion thereof is recycled to a suitable location in the reactor. Generally, the medium or stream that is cooled in the cooler enters the cooler at a temperature of from about 150° to about 220° C. (302 to 428° F.) and exits the cooler at a temperature of from about 140° to about 190° C. (284–374° F.).

The cooler can be any suitable indirect heat exchanger. By indirect heat exchange as used herein it is meant that the heat is transferred from one process stream to another process stream without direct contact of the two streams. In addition, indirect heat exchange means that the heat exchanges from one process stream to another process stream without going through an intermediate heat transfer fluid, such as a utility stream such as boiler feed water or stream, such as is practiced in the prior art processes. A shell and tube heat exchanger is preferred, with the portion of the reaction medium or reaction solution on the tube side of the exchanger. Preferably, the pressure drop across the tube side of the exchanger is minimized. After cooling, the cooled reaction medium or reaction solution reactor effluent stream is recycled to the inlet of the reaction section of the reactor.

In another embodiment of this invention, the reactor is not a 3PTR but may instead be a CSTR, a slurry reactor, an ebullated bed reactor, or even a fixed bed reactor. The common characteristic of the reactors in this embodiment is that the bed as a whole does not move. The reactor comprises a plurality of pipes connected in parallel containing the reaction medium. The pipes are surrounded by a sheath into which the other process stream flows for heat exchange. The pipes and sheath thus form an internal heat exchanger that is within the reaction zone and by which heat can be indirectly exchanged from the reaction medium to the other process stream. A suitable reactor for this embodiment is shown in U.S. Pat. No. 5,520,890 (Lorentzen et al).

During the course of carbonylation reactions, a liquid reaction effluent stream exits from the separation section of a 3PTR and flows to a flash zone. Between the 3PTR and the flash zone, the stream generally undergoes a pressure reduction. This reduction in pressure vaporizes some of the liquid stream into a gas, thereby cooling the liquid stream. The pressure reductions can occur in one or more stages. Likewise, the flashing can occur in one or more stages. Thus, it is within the scope of this invention that the stream flowing from the separation zone passes serially through a train of pairs of pressure reductions and flashes.

The magnitude of the pressure reduction, and of the resultant temperature decrease, depends on a number of factors, including the desired carboxylic acid product, the temperature and pressure in the carbonylation reaction zone, and the composition of the liquid stream flowing from the reaction zone to the flash zone. For acetic acid production, the carbonylation reaction zone generally operates at a temperature of from about 150° to about 220° C. (302° to 428° F.) and at a pressure of generally from about 25 to about 60 kg/cm$^2$(g) (356 to 853 psi(g)), and preferably about 35 to about 45 kg/cm$^2$(g) (498 to 640 psi(g)), while the flash zone operates at a pressure of generally from about 0 to about 7 kg/cm$^2$(g) (0 to 100 psi(g)), and preferably about 0 to about 3.5 kg/cm$^2$(g) (0 to 50 psi(g)). For the production of other carboxylic acids, persons of ordinary skill in the art are able to compute the resultant decrease in temperature that occurs for a particular liquid stream composition as a result of a given pressure reduction between the reaction and flash zones.

The pressure reduction between the reaction zone and the flash zone improves the differential temperature driving force for exchanging heat according to this invention. This is because the reduction in pressure vaporizes some of the liquid stream into a gas, thereby cooling the liquid stream. This temperature decrease is critical, because it provides the differential temperature driving force for heat to be exchanged from the heat exchanger to the other stream in the process. Generally, the stream that is heated by the heat exchanger, or cooler, enters at a temperature of from about 130° to about 180° C. (266° to 356° F.) and exits at a temperature of from about 140° to about 190° C. (284° to 374° F.).

It is useful at this point to define the term, "attrited solid catalyst particles." As used herein, "attrited solid catalyst particles" means solid catalyst particles that have undergone mechanical attrition and/or thermal attrition. Mechanical attrition means the transformation of larger catalyst particles into smaller catalyst particles in the absence of a change in the chemical composition of the catalyst particles. Examples include breakage and fracturing that occur during transport, which can yield chips, pieces, fines, or other fragments of the solid catalyst particles. Thermal attrition means the transformation of catalyst particles that occurs as a result of exposure to elevated temperature and that does result in a change in the chemical composition of the catalyst particles. With polyvinylpyridine resin, for example, thermal attrition includes the breakdown of the cross-linkages within the polyvinylpyridine resin and the breakdown of the linkages comprising the backbone of the polyvinylpyridine resin. The term "thermal attrition," however, is not meant to include the plasticization or melting of the resin, the decomposition of the resin into a gum, the decomposition of the resin into a soft coke, or the complete depolymerization of the resin. Attrited solid catalyst particles tend to severely foul equipment. When a liquid-solid reaction effluent that contains attrited solid catalyst particles flows through equipment such as flash drums and heat exchangers wherein the liquid phase is at least partially vaporized, the attrited solid catalyst particles can form a tar-like deposit that can interfere with the performance of this equipment.

The temperature of the flash zone is generally less than the temperature at which rapid thermal attrition of the solid catalyst particles occurs. Thus, the maximum temperature of the flash zone depends on several factors, including the susceptibility of the solid catalyst to attrit thermally, as well as the ability or inclination of the owner or operator of a carbonylation process to deal with a given rate of thermal attrition. However, it is believed that, for solid catalyst particles comprising resins such as polyvinylpyridine and polyvinylpyrrolidone, the maximum temperature of the flash zone is generally less than about 220° C. (428° F.), preferably less than about 200° C. (392° F.), and more preferably less than about 180° C. (356° F.). For the production of acetic acid, the flash zone preferably operates at a temperature of from about 105° to about 165° C. (221° to 329° F.).

The pressure reduction of the liquid stream enroute to the flash zone facilitates the separation of the entering liquid components from the solid catalyst particles. In general, the greater the reduction in pressure between the reaction zone and the flash zone, the greater is the resultant degree of separation between the liquids and solids in the flash zone. Although in theory operating the flash zone at a subatmospheric pressure would further improve the extent of liquid-solid separation, capital expenses, operating expenses, and practical complications associated with operating the flash zone at a vacuum far outweigh the benefits of a further decrease in the temperature of the liquid stream.

In general, the flash zone may be any suitable device for separation of liquids from solid catalyst particles. In its simplest form, the flash zone may be an empty vessel in which liquid and vapors, which are both entrained and a result of the pressure reduction, separate subject to the momentum of the entering liquid stream and under the force of gravity. However, to facilitate the separation, the flash zone preferably uses a packed section located between the inlet nozzle and the vapor outlet nozzle.

Although not a requirement of this invention, it is preferred that the flash zone comprise a packed section. The packed section helps to intercept upflowing solid catalyst particles, attrited solid catalyst particles, including catalyst chips and fines, and heavy by-products that are carried upward with the gaseous or vaporous components toward the vapor outlet of the flash zone. The packed section provides a surface that a liquid wash stream can irrigate in order to flush the attrited solid catalyst particles and heavy by-products downward toward the solid outlet of the flash drum. Generally at least 95 wt-%, and preferably at least 99.9 wt-% of the attrited solid catalyst particles and heavy by-products that enter the flash zone are captured and exit the flash zone through the solids outlet, rather than through a liquid or vapor outlet. The packed section contains any suitable packing which may be one or more dumped packings and/or one or more arranged or structured packings. Suitable dumped packings include rings (i.e., Raschig or pall) and saddles (i.e., berl or intalox), and suitable arranged packings include Flexipac (known also as Mellapak) which is formed from lamellar or corrugated sheet metal. The packing material can be metallic, ceramic, or glass.

The flash zone may or may not have a reboiler, for it is not a requirement of this invention that the flash zone have a reboiler. However, the flash zone preferably has a reboiler, and in such a case it is within the scope of one embodiment of this invention that the reaction medium or the reaction solution exchanges heat in the reboiler and thus provides some or all of the heat required for reboiling the flash zone. Whether the flash zone has a reboiler depends on a number of factors, including the composition of the reaction solution, in particular the concentrations of alkyl iodide and/or of byproducts such as methyl acetate in the reaction solution. In the case of the production of acetic acid, the concentration of methyl iodide in the reaction solution is generally from about 5 to about 20 wt-%, typically from about 10 to about 15 wt-%, and preferably from about 13 to about 14 wt-%, of the reaction solution, and the concentration of methyl acetate in the reaction solution is generally from about 0.5 to about 30 wt-%, typically from about 1 to about 4 wt-%, and preferably from about 2 to about 4 wt-%, of the reaction solution. In some acetic acid processes, the concentration in the reaction solution of methyl acetate is between about 10 and about 25 wt-% of the reaction solution. In general, within these ranges of concentrations the greater the concentration of methyl iodide, or of methyl acetate, the more practical it is for the flash zone to have a reboiler.

Other factors that determine whether the flash zone has a reboiler include the compositions and the flow rates of the external reflux to the flash zone, if any, and of the wash fluid to the flash zone. The flow rate of the wash fluid to the flash zone is influenced by a number of factors including the flow rates of liquid, gas, entrained solid catalyst particles, and entrained attrited solid catalyst particles entering the flash zone; the cross-sectional area of the flash zone; the surface area of the packing of the flash zone; the nature of the particles (i.e., their tackiness or adherence) entering the flash zone; and the wetting characteristics of any packing in the flash zone. The flow rate of the wash fluid is generally between about 1 and about 25 wt-%, and preferably between about 6 and about 14 wt-%, of the sum of the net draw of water and the net draw of acetic acid from the flash zone. For purposes of computing this flow rate of wash fluid, the net draw of water is computed by adding the water in each net stream withdrawn from the flash zone, and the net draw of acetic acid is computed by adding the acetic acid in each net stream withdrawn from the flash zone. The net draw of water, or the net draw of acetic acid, may be withdrawn via more than one stream.

The stream that is used to exchange heat with the reaction medium or the reaction solution in the cooler is a stream comprising the desired carboxylic acid product. Any such stream in the process that requires heat and that is at a temperature suitable for exchanging heat with the reaction medium or reaction solution is suitable. In the event that the quantity of heat that is needed to be removed from the reaction zone is greater than the heat that is required for the other process stream, then a trim cooler can be used to cool the reaction medium or reaction solution to an additional extent. On the other hand, if the quantity of heat that is needed to be added to the other process stream is greater than the heat that is available to be removed from the reaction zone, then a trim heater can be used to heat the other process stream to the desired additional degree.

Generally, suitable streams for exchanging heat with the reaction medium or the reaction solution include portions of the bottoms streams of columns that purify the reaction effluent. These streams generally contain the product carboxylic acid, and furthermore they generally have a concentration of the product carboxylic acid that is not less than that in the reactor effluent. Thus, in one embodiment of this invention where the reaction effluent passes to a flash zone to remove light ends, a portion of the bottoms stream of the flash zone may be reboiled by heat exchange with the reaction medium or the reaction solution. In another embodiment of this invention, a sidedraw stream containing the product carboxylic acid is withdrawn from the flash zone and passes to a dehydration column for water removal. The dehydration column bottom temperature is usually from about 10° to about 50° C. (18° to 90° F.), and typically from about 20° to about 40° C. (18° to 72° F.), higher than the boiling point of the desired carboxylic acid product at the operating pressure of the dehydration column. In this other embodiment, the reaction medium or the reaction solution exchanges heat with a stream from the dehydration column bottoms, which returns to the dehydration column to reboil the dehydration column. In yet another embodiment, a dehydration column bottoms stream containing carboxylic acid product passes to a finishing column for removal of heavy byproducts. The finishing column bottom temperature is usually from about 10° to about 50° C. (18 to 90° F.), and more typically from about 20° to about 40° C. (18 to 72° F.), higher than the boiling point of the desired carboxylic acid product at the operating pressure of the finishing column. In this embodiment, a stream from the finishing column bottoms exchanges heat with the reaction medium or the reaction solution and recycles to the finishing column in order to reboil the finishing column. In each of these embodiments, if sufficient heat is transferred, then the need to provide heat from a source that is external to the process for the purpose of reboiling the zone or the column may be minimized or even eliminated. In the production of acetic acid, the bottom temperatures of the dehydration and finishing columns are preferably from about 140° to about 150° C. (284°–302° F.).

Figure 2:
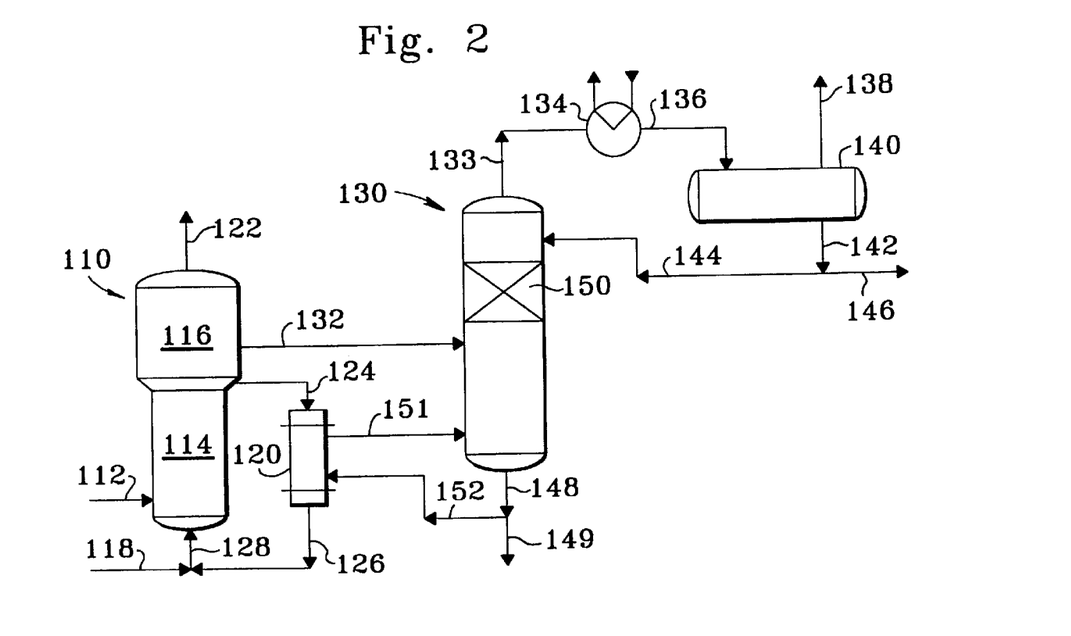
FIGS. 2 and 3 depict flow diagrams of two other embodiments of the invention.
Figure 3:
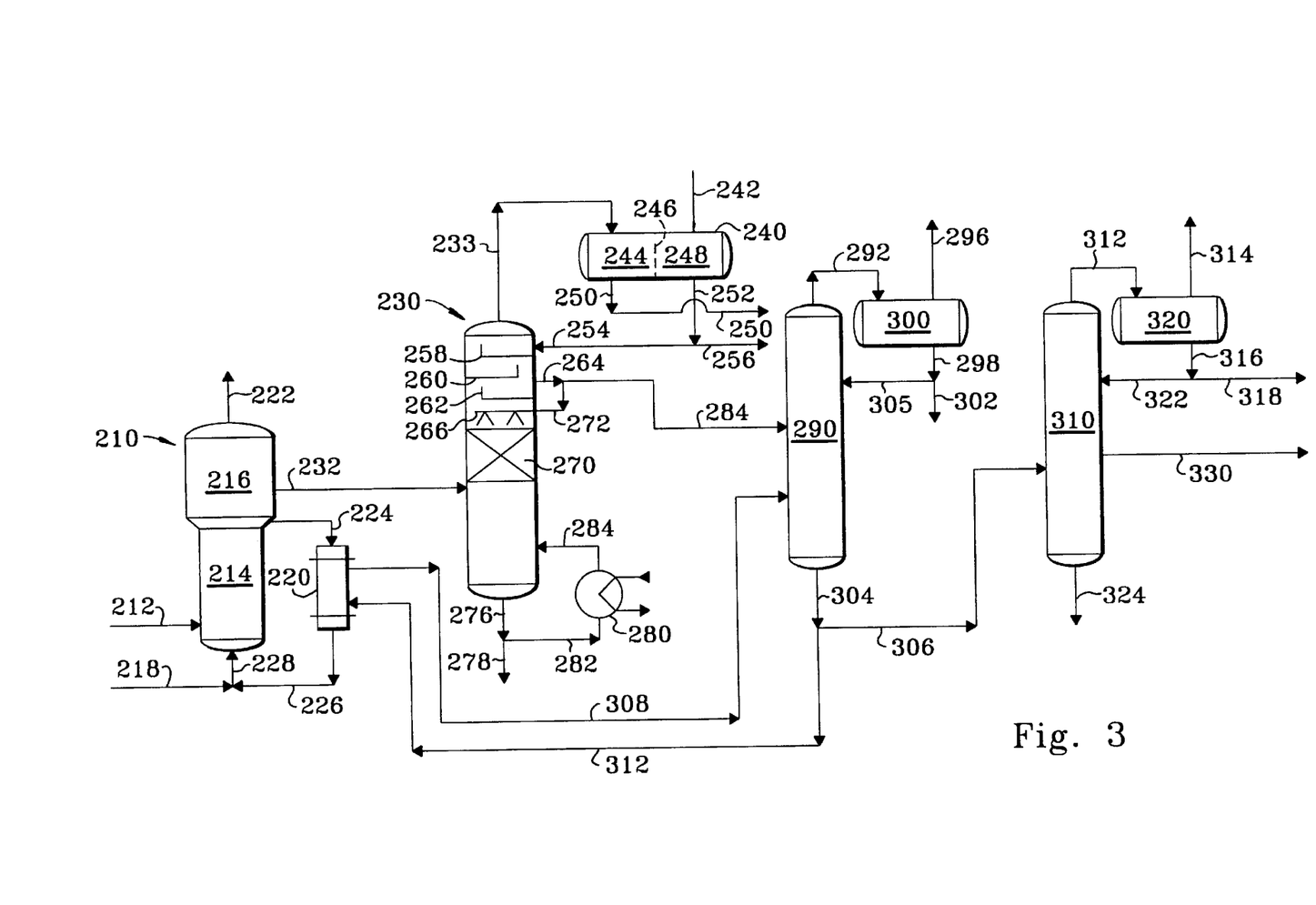

FIGS. 1, 2, and 3 will now be used in describing three specific embodiments of the invention. The most widely practiced carbonylation process to which the present invention is applicable is the carbonylation of methanol with carbon monoxide to produce acetic acid. Therefore, the Figures will be described in terms of their application to an acetic acid production process. It is not intended that this description or these embodiments limit the broad scope of the invention as presented in the claims. The Figures show only elements and equipment which are essential to a clear understanding of the invention.

FIG. 1 illustrates a carbonylation 3PTR, which is generally denoted as 10, with a lower reaction section 14 and an upper separation section 16. A feed stream containing methanol in the liquid phase enters the process through a line 18 and combines with a recycle slurry stream flowing through a line 26. The recycle slurry stream contains solid catalyst particles and the reaction solution. The combined stream of methanol and recycled slurry passes through a line 28 and enters the reaction section 14 of the reactor 10. A feed stream containing carbon monoxide in the gas phase also enters reactor 10 through a line 12. In the reaction section 14, carbon monoxide, which is provided in a molar excess, reacts with methanol to produce acetic acid via carbonylation in the presence of the catalyst particles while the gas-liquid-solid reaction medium is transported upward in the 3PTR. As used herein, the term "reaction medium within the reactor" is intended to mean the combination of reaction solution and catalyst particles which is present in the reactor at any point in time in the course of the reaction. The reaction medium generally comprises carbon monoxide, methanol, acetic acid, and solid catalyst particles. In addition, the reaction medium may contain a catalytic promoter, such as an alkyl halide like methyl iodide, which is necessary for some solid catalyst particles. The reaction medium may also contain side reaction by-products such as water and methyl acetate. The presence of methyl acetate can be explained as the corresponding ester that results from the esterification of the alcohol and the product acetic acid. Heavy by-products of side reactions, such as propionic acid and acids having 3 or more carbon atoms, may also be present.

At the top of the reaction section 14, the upflowing reaction medium enters the separation section 16 where the gas, liquid, and solid components of the reaction medium disengage to some extent. To aid disengagement, the separation section 16 generally has a larger cross-section than the reaction section 14 and contains baffles and other internal devices. Gaseous components such as unreacted carbon monoxide exit the separation section 16 through a line 22. These gaseous components can be recycled to the reaction section 14 by means not shown in FIG. 1. Liquids such as acetic acid, methyl acetate, methyl iodide, propionic acid, and any unreacted methanol, along with both soluble gases and entrained solid catalyst particles in the liquid, exit the separation section 16 through a line 32.

A slurry of solid catalyst particles with entrained liquids and some soluble gases exits through a line 24. At the conditions of reaction section 14, the carbonylation of methanol to acetic acid is an exothermic reaction. The exothermic heat of reaction, as computed from standard heats of formation at 25° C. (77° F.) of gaseous carbon monoxide, liquid methanol, and liquid acetic acid, is about 33 kcal/g-mole (137 kJ/g-mole). This heat of reaction is removed by cooling the slurry flowing through the line 24 in the cooler 20. The cooling medium is an acetic acid containing stream flowing in a line 36 from a separation zone 30. The cooled slurry flows through the line 26 and combines with the methanol feed stream in the line 18, as previously described. The heated acetic acid containing stream flows through a line 38 and reenters the separation zone 30.

The function of separation zone 30 is to remove light materials from the reaction effluent flowing in the line 32. Such light materials may include carbon monoxide, water, methyl acetate, methyl iodide, and any unreacted methanol. A portion of the stream flowing in the line 32 may be recycled to the reaction section 14. A stream having a decreased concentration of these light materials, and hence an increased concentration of acetic acid, relative to the reaction effluent is withdrawn from the separation zone 30 via a line 34. The previously mentioned stream flowing through the line 36 to the cooler 20 is an aliquot portion of the stream flowing in the line 34. The remainder of the stream flowing in the line 34 passes through a line 40 to further product recovery and purification facilities, which are not shown in FIG. 1.

Referring now to FIG. 2, equipment and lines in FIG. 2 that are similar to those in FIG. 1 and that have already been described in detail in the context of FIG. 1 will be described only briefly here in order to avoid needless repetition. Looking now to FIG. 2, carbonylation 3PTR denoted as 110 has a lower reaction section 114 and an upper separation section 116. Liquid methanol enters through line 118 and mixes with a recycle slurry stream in line 126. The combined methanol-slurry stream passes through line 128 into reaction section 114. Gaseous carbon monoxide enters reactor 110 through line 112. Carbon monoxide reacts with methanol to make acetic acid in reaction section 114.

At the top of reaction section 114, the upflowing reaction medium enters separation section 116. Gaseous carbon monoxide exits through a line 122. Liquids such as acetic acid, methyl acetate, methyl iodide, propionic acid, and any unreacted methanol, along with both soluble gases and entrained solid catalyst particles in the liquid, exit through a line 132. A slurry of solid catalyst particles with entrained liquids and some soluble gases exits through a line 124. Cooler 120 cools the slurry using a portion of the bottom stream of a flash drum 130. The cooled slurry flows through the lines 126 and 128 to the reaction section 114.

The stream in line 132 is depressured and enters flash drum denoted as 130. On entering the flash drum 130, a portion of the stream flowing through the line 132 flows upward and into a packed section 150 of the flash drum 130. The packed section 150 is a counter-current contacting zone, in which upward flowing light components materials contact a downward flowing liquid in order to remove solid catalyst particles, attrited solid catalyst particles, and heavy by-products. The light materials that are carried upward through the packed section 150, to the top of the flash drum 130, and through a line 133 include carbon monoxide, water vapor, methyl acetate, methyl iodide, acetic acid vapor, as well as any unreacted methanol vapor. These upward flowing light materials carry solid catalyst particles, attrited solid catalyst particles, and heavy by-products, which are intercepted by the packing in the packed section 150 and are irrigated toward the bottom of the flash drum 130 by the downward flowing wash liquid.

Condenser 134 condenses most of the acetic acid, any unreacted methanol, methyl iodide, and methyl acetate, as well as some of the water, in the stream flowing through the line 133. A two-phase vapor-liquid stream flows through a line 136 and enters a receiver 140. The receiver 140 is particularly well-suited for separating noncondensed components from a single liquid phase as opposed to from two liquid phases. Such a single liquid phase can be produced in the receiver 140 when the receiver conditions are such that the amount of condensed methanol and/or acetic acid in the receiver 140 is sufficient to solubilize in a single phase not only the water but also the methyl acetate and methyl iodide present in the receiver 140. Noncondensed components, such as carbon monoxide, exit the receiver 140 through a line 138, and can be recycled to the reaction section 114 by means not shown in FIG. 2. The condensed liquids exit the receiver 140 through a line 142. A portion of the condensed liquids is withdrawn through a line 146 and passed to further downstream separation facilities, which are not shown in FIG. 2. Such facilities are known to persons of ordinary skill in the art and do not require detailed description herein. These separation facilities can comprise means for recycling methyl acetate and methyl iodide to the reaction section 114, for rejecting water from the process, and for recovering acetic acid product.

Another portion of the condensed liquid flowing through the line 142 passes through a line 144 and enters the flash drum 130 at a point above the packed section 150. A distributor (not shown in FIG. 2) can be used to ensure that the condensed liquid is distributed uniformly across the entire cross-section of the packed section 150. The condensed liquid flows downward through the packing, and countercurrent to the upward flowing components described previously.

The liquid that exits the bottom of the packed section 150 contains the attrited solid catalyst particles and heavy by-products that were removed from the upflowing vapors. These liquids and solids leave the flash drum 130 through a line 148. The solids content of the stream flowing in the line 148 is generally less than 25 wt-%, and preferably less than 10 wt-%, in order to ensure that the stream becomes neither too solids-rich so as to foul and plug equipment nor too viscous so as to be unable to be pumped freely. A portion of the stream in the line 148 flows through a line 152, is heated in the cooler 120, and passes to the flash drum 130 via a line 151. Another portion of the stream in the line 148 passes through a line 149 and is recycled to the reaction section 114 by means not shown in FIG. 2.

FIG. 3 illustrates an embodiment of the invention in which a portion of an acetic acid containing bottom stream from a dehydration column is the cooling medium in the cooler that removes the heat of reaction from the carbonylation reactor. In addition, vapor-liquid contacting trays are located in the flash drum between the packing section and the vapor outlet, and there are two net liquid streams from the flash drum receiver. This is in contrast to FIG. 2, where there are no vapor-liquid contacting trays in the flash drum and where there is only one net liquid stream from the receiver. Equipment and lines in FIG. 3 that are similar to those in FIGS. 1 and 2 and that have already been described in detail in the context of FIGS. 1 and 2 will be described only briefly here.

Looking now to FIG. 3, carbonylation 3PTR, 210, has a reaction section 214 and an separation section 216. Methanol enters via line 218 and mixes with a recycled slurry in line 226. The methanol-slurry combined stream flows passes via line 228 to reaction section 214. Carbon monoxide enters reaction section 214 via line 212. The reaction medium enters separation section 216. Carbon monoxide leaves line 222. Liquids with soluble gases and entrained solid catalyst particles exit through a line 232. A catalyst particle slurry exits via line 224 and is cooled in cooler 220 using a portion of the bottom stream of a dehydration column 290. The cooled slurry flows via lines 226 and 228 to reaction section 214.

The stream in line 232 is depressured and enters flash drum 230. A portion of the steam in line 232 flows upward and into packed section 270. Packed section 270 helps to remove solid catalyst particles, attrited solid catalyst particles, and heavy by-products by countercurrent contacting with a downflowing liquid wash stream. The liquid wash stream is produced using the previously mentioned vapor-liquid contacting trays. Three vapor-liquid trays 258, 260, and 262 are shown in FIG. 3, but there may be more trays.

A liquid crude acetic acid stream is withdrawn via line 264 from tray 262, and a portion is recycled via line 272 and distributor 266 to packed section 270 as liquid wash. The remaining portion of the liquid crude acetic acid stream, which contains water, flows through a line 284 to the dehydration column 290.

Line 233 carries a vapor stream comprising carbon monoxide, water vapor, methyl acetate, and methyl iodide vapor. This vapor stream is partially condensed in a condenser (not shown) and enters receiver 240, with baffle 246 and compartments 244 and 248. The receiver 240 is particularly well-suited for separating noncondensed components from two liquid phases as opposed to from a single liquid phase. Two liquid phases can form in the receiver 240 when the receiver conditions are such that the amount of condensed methanol and/or acetic acid in the receiver 240 is not sufficient to solubilize in a single phase all of the methyl acetate, methyl iodide, and water. Under these conditions, a water-rich phase comprising water, acetic acid, and the trace amount of methyl acetate and methyl iodide, and a water-poor phase comprising methyl acetate, methyl iodide, and trace amounts of water and acetic acid are formed. As used herein, the term water-rich means having a concentration of water of equal to or greater than 40 wt-% and water-poor means having a concentration of water of less than 40 wt-%.

The water-poor phase collects in compartment 244 and flows via a line 250 to facilities (not shown) for at least partial recycling to reaction section 214. The water-rich phase collects in compartment 248 and is withdrawn through a line 252, of which a portion is refluxed to flash drum 230 via line 254. The remainder of the water-rich phase flows via line 256 to facilities (not shown) for at least partial recycling to reaction section 214. Vaporous carbon monoxide, water, methyl acetate, and methyl iodide are sent from receiver 240 via line 242 to facilities (not shown) for recycling at least the carbon monoxide to reaction section 214.

Solid catalyst particles, attrited solid catalyst particles, and heavy by-products in a liquid stream leave the flash drum 230 through a line 276. A portion of the stream in the line 276 flows through a line 282, is heated in a reboiler 280, and passes to the flash drum 230 via a line 284. Another portion of the steam in the line 276 passes through a line 278 and is recycled to the reaction section 214 by means not shown in FIG. 3.

Dehydration column 290 is a trayed fractionation column that removes water from the entering liquid crude acetic acid stream. Water-containing vapors pass through a line 292, and after condensing collect in receiver 300. Nonconden-sibles vent via a line 296, and the water-containing condensate is withdrawn through a line 298. Some of the condensate is refluxed to the column 290 via a line 305, and the remainder is recovered via line 302. A dry acetic acid stream is withdrawn via line 304 from the bottom of dehydration column 290. One portion flows through a line 312 and functions as the medium in cooler 220 for cooling the catalyst slurry. Cooler 220 heats the dry acetic acid stream, thereby serving the function of a reboiler for dehydration column 290. The heated dry acetic acid stream returns to column 290 via line 308.

Another portion of the dry acetic acid stream flows through a line 306 to a finishing column 310 for removal of heavy by-products, principally propionic acid. Column 310 is a trayed fractionation column that produces a bottoms steam rich in propionic acid that is rejected from the process via line 324. Vapors comprising intermediate boiling impurities and byproducts are withdrawn from column 310 via line 312, and are condensed and collected in receiver 320. Noncondensible gases are vented via line 314. An overhead liquid stream flows from receiver 320 via line 316. One portion serves as reflux for column 310 via line 322, and the other portion in line 318 is an overhead liquid drag stream to purge impurities and by-products from column 310. At least a portion of the drag stream can be recycled to the process. A refined acetic acid product stream is withdrawn from the column 310 as a sidedraw in the line 330.

What is claimed is:

1. A process for the production of a carboxylic acid, the process comprising the steps of:
   a) reacting (i) an alcohol and/or a reactive derivative of an alcohol and (ii) carbon monoxide in the presence of solid catalyst particles in a reaction zone to produce carboxylic acid, and recovering from the reaction zone a first reaction effluent comprising carboxylic acid and a second reaction effluent comprising carboxylic acid;
   b) cooling the first reaction effluent in an effluent recycle heat exchanger to produce a recycle stream, and passing at least a portion of the recycle stream to the reaction zone;
   c) separating the second reaction effluent in a separation zone, and withdrawing from the separation zone a heavy stream comprising carboxylic acid;
   d) heating at least a portion of the heavy stream by indirect heat exchange in the effluent recycle heat exchanger with the first reaction effluent to produce a heated heavy stream;
   e) passing at least a portion of the heated heavy stream to the separation zone; and
   f) recovering carboxylic acid from the separation zone.

2. The process of claim 1 further characterized in that the separation zone comprises a flash zone, a bottom stream comprising carboxylic acid is withdrawn from the flash zone, and the heavy stream comprises the bottom stream.

3. The process of claim 1 wherein the recovering of carboxylic acid from the separation zone comprises recovering carboxylic acid from the heavy stream or the heated heavy stream.

4. The process of claim 1 wherein the second reaction effluent comprises carbon monoxide, water, an ester corresponding to the esterification of the alcohol and the carboxylic acid, heavy by-products, and solid catalyst particles, and further characterized in that the separating of the second reaction effluent in the separation zone comprises:
   a) passing the second reaction effluent to a flash zone;
   b) withdrawing from the flash zone a flash overhead stream comprising carbon monoxide, water, ester, and carboxylic acid and a flash bottom stream comprising carboxylic acid, heavy by-products, and solid catalyst particles;
   c) recycling at least a portion of the flash bottom stream to the reaction zone;
   d) passing the flash overhead stream to a dehydration column, separating the flash overhead stream in the dehydration column, and withdrawing from the dehydration column a dehydration overhead stream comprising carbon monoxide, water, and ester, and a dehydration bottom stream comprising carboxylic acid and heavy by-products; and
   e) passing the dehydration bottom stream to a finishing column, separating the dehydration bottom stream in the finishing column, and withdrawing from the finishing column a finishing overhead stream comprising carboxylic acid and a finishing bottom stream comprising heavy by-products.

5. The process of claim 4 further characterized in that the heavy stream comprises at least a portion of the flash bottom stream.

6. The process of claim 4 further characterized in that the heavy stream comprises at least a portion of the dehydration bottom stream.

7. The process of claim 4 further characterized in that the heavy stream comprises at least a portion of the finishing bottom stream.

8. The process of claim 1 further characterized in that a common reaction effluent comprising carboxylic acid is withdrawn from the reaction zone and wherein the first reaction effluent comprises an aliquot portion of the common reaction effluent and the second reaction effluent comprises an aliquot portion of the common reaction effluent.

9. The process of claim 1 further characterized in that the first reaction effluent comprises solid catalyst particles, solid catalyst particles are cooled in the effluent recycle heat exchanger, and the recycle stream comprises solid catalyst particles.

10. The process of claim 1 further characterized in that the first reaction effluent enters the effluent recycle heat exchanger at a temperature of from about 150° C. to about 220° C.

11. The process of claim 1 further characterized in that the recycle stream leaves the effluent recycle heat exchanger at a temperature of from about 140° C. to about 190° C.

12. The process of claim 1 further characterized in that the at least a portion of the heavy stream enters the effluent recycle heat exchanger at a temperature of from about 130° C. to about 180° C.

13. The process of claim 1 further characterized in that the heated heavy stream leaves the effluent recycle heat exchanger at a temperature of from about 140° C. to about 190° C.

14. The process of claim 1 wherein the solid catalyst particles comprise a polyvinylpyridine resin.

15. The process of claim 1 wherein the solid catalyst particles comprise a polyvinylpyrrolidone resin.

16. The process of claim 1 further characterized in that the alcohol comprises methanol and the carboxylic acid comprises acetic acid.

17. A process for the production of a carboxylic acid, the process comprising the steps of:
   a) reacting (i) an alcohol and/or a reactive derivative of an alcohol and (ii) carbon monoxide in the presence of solid catalyst particles in a reaction zone to produce carboxylic acid, withdrawing from the reaction zone a reaction effluent comprising carboxylic acid, and withdrawing from the reaction zone a recirculation stream comprising carboxylic acid;
   b) cooling at least a portion of the recirculation stream in an effluent recycle heat exchanger to produce a recycle stream, and passing at least a portion of the recycle stream to the reaction zone;
   c) separating the reaction effluent in a separation zone, and withdrawing from the separation zone a heavy stream comprising carboxylic acid;
   d) heating at least a portion of the heavy stream by indirect heat exchange in the effluent recycle heat exchanger with the at least a portion of the recirculation stream to produce a heated heavy stream;
   e) passing at least a portion of the heated heavy stream to the separation zone; and
   f) recovering the carboxylic acid from the separation zone.

18. The process of claim 17 further characterized in that the recirculation stream comprises solid catalyst particles.

19. A process for the production of a carboxylic acid, the process comprising the steps of:
- a) reacting (i) an alcohol and/or a reactive derivative of an alcohol and (ii) carbon monoxide in a reaction zone to produce carboxylic acid, wherein the reacting is in the presence of a reaction medium comprising solid catalyst particles, alcohol and/or the reactive derivative thereof, and carboxylic acid, and withdrawing from the reaction zone a reaction effluent comprising carboxylic acid;
- b) cooling at least a portion of the reaction medium in an internal heat exchanger in the reaction zone;
- c) separating the reaction effluent in a separation zone, and withdrawing from the separation zone a heavy stream comprising carboxylic acid;
- d) heating at least a portion of the heavy stream by indirect heat exchange in the internal heat exchanger with the at least a portion of the reaction medium to produce a heated heavy stream;
- e) passing at least a portion of the heated heavy stream to the separation zone; and
- f) recovering the carboxylic acid from the separation zone.

* * * * *